(12) United States Patent
Wakamoto et al.

(10) Patent No.: US 9,139,807 B2
(45) Date of Patent: Sep. 22, 2015

(54) CELL CULTURE APPARATUS, APPARATUS FOR LONG-TERM OBSERVATION OF CELL CULTURE, METHOD FOR LONG-TERM CELL CULTURE, AND METHOD FOR LONG-TERM OBSERVATION OF CELL CULTURE

(75) Inventors: Yuichi Wakamoto, Tokyo (JP); Mikihiro Hashimoto, Tokyo (JP)

(73) Assignee: JAPAN SCIENCE AND TECHNOLOGY AGENCY, Saitama (JP)

( * ) Notice: Subject to any disclaimer, the term of this patent is extended or adjusted under 35 U.S.C. 154(b) by 0 days.

(21) Appl. No.: 14/130,122

(22) PCT Filed: Jul. 13, 2012

(86) PCT No.: PCT/JP2012/068005
§ 371 (c)(1),
(2), (4) Date: Dec. 30, 2013

(87) PCT Pub. No.: WO2013/011962
PCT Pub. Date: Jan. 24, 2013

(65) Prior Publication Data
US 2014/0147879 A1 May 29, 2014

(30) Foreign Application Priority Data
Jul. 15, 2011 (JP) ................................. 2011-156767

(51) Int. Cl.
| | | |
|---|---|---|
| *C12M 1/00* | (2006.01) | |
| *C12Q 1/06* | (2006.01) | |
| *C12Q 1/24* | (2006.01) | |
| *C12M 1/34* | (2006.01) | |
| *C12Q 1/04* | (2006.01) | |
| *C12Q 1/02* | (2006.01) | |
| *C12M 3/06* | (2006.01) | |
| *C12M 1/12* | (2006.01) | |

(52) U.S. Cl.
CPC ............... *C12M 41/46* (2013.01); *C12M 23/16* (2013.01); *C12M 23/22* (2013.01); *C12M 23/34* (2013.01); *C12M 23/40* (2013.01); *C12M 25/02* (2013.01); *C12M 29/10* (2013.01); *C12M 41/36* (2013.01); *C12Q 1/02* (2013.01); *C12Q 1/045* (2013.01)

(58) Field of Classification Search
CPC ........ C12M 3/00; C12M 23/02; C12M 23/16; C12N 5/06; C12N 5/0602; C12N 2535/00; C12N 2537/00; C12N 2539/00; C12N 2533/10; C12N 2533/50; C12N 2533/54; C12N 1/00; C12N 1/04; C12N 1/20; B01L 1/00; B01L 3/56; B01L 3/561; G01N 1/00; G01N 1/2035; G01N 1/20; G01N 1/18; G01N 1/10; G01N 1/38; C12Q 1/00; C12Q 1/04; C12Q 1/06; C12Q 1/24

See application file for complete search history.

(56) References Cited

U.S. PATENT DOCUMENTS

| 2004/0067482 A1* | 4/2004 | Yasuda et al. ..................... 435/4 |
| 2007/0161106 A1* | 7/2007 | Jervis et al. .................. 435/325 |

FOREIGN PATENT DOCUMENTS

| JP | 2002-153260 | 5/2002 |
| JP | 2005-333912 | 12/2005 |
| JP | 2006-57 | 1/2006 |
| JP | 2008-199919 | 9/2008 |
| WO | 02/42411 | 5/2002 |

OTHER PUBLICATIONS

Wang, P. et al. 2010. Robust growth of *Escherichia coli*. Current Biology 20: 1099-1113.*
International Search Report issued Sep. 11, 2012 in International (PCT) Application No. PCT/JP2012/068005.
Notification of Reasons for Refusal issued Jan. 9, 2013 in Japanese Application No. 2012-552173, with English translation.
Decision to Grant a Patent issued Mar. 7, 2013 in Japanese Application No. 2012-552173, with English translation.
Wang et al., "Robust Growth of *Escherichia coli*", Current Biology, vol. 20, Jun. 22, 2010, pp. 1099-1103.

* cited by examiner

*Primary Examiner* — John S Brusca
*Assistant Examiner* — Sharon M Papciak
(74) *Attorney, Agent, or Firm* — Wenderoth, Lind & Ponack, L.L.P.

(57) ABSTRACT

Provided is a cell culture apparatus, an apparatus for long-term observation of cell culture, a method for long-term cell culture, and a method for long-term observation of cell culture, which are capable of continuously culturing and observing cells under uniform environmental conditions without aging of the cultured cells' physiological state, and also tracing the history of a cell. The cell culture apparatus comprises a cell culture substrate, a semipermeable membrane, and a culture solution supplier. The cell culture substrate has on a surface a narrow culture groove for holding and culturing cells and wide flow grooves for discarding the cells held and cultured in the culture groove. Both ends of the culture groove are connected to the flow grooves being larger in width and depth than the culture groove. The semipermeable membrane covers the culture groove and the flow grooves. Finally, the culture solution supplier continuously supplies culture solution.

13 Claims, 16 Drawing Sheets

(A)

(B)

(C)

(A)

(B)

(A)

(B)

CELL CULTURE APPARATUS, APPARATUS FOR LONG-TERM OBSERVATION OF CELL CULTURE, METHOD FOR LONG-TERM CELL CULTURE, AND METHOD FOR LONG-TERM OBSERVATION OF CELL CULTURE

TECHNICAL FIELD

The present invention relates to a cell culture apparatus, an apparatus for long-term observation of cell culture, a method for long-term cell culture, and a method for long-term observation of cell culture.

BACKGROUND ART

Conventionally, it was difficult to continuously culture and observe cells placed in a container such as cell culture dish over many generations under a microscope because cells consume nutrition, waste products accumulate, and the environment around cells varies with the lapse of time. Furthermore, proliferation increases the number of cells in a container exponentially, which makes tracking and observing a certain cell difficult.

Thus, the present inventors proposed a method for long-term culture of cells, for example, in which the cells are placed in a micrometer-size container and a part of the cells is removed out of the measurement system using a cell handling technique such as an optical tweezer (Non-patent document 1). However, in this method, since only a small number of cells can be transferred at one time and the experimenter has screen all the cells individually for removal, the work involves a great burden and the continuous culture has been practically limited to about ten generations at most.

On the other hand, a method called "mother machine" has recently attracted attentions as a method for long-term culture and observation of cells (Non-patent document 2). In this method, wide grooves (100 μm width) and narrow whisker-like grooves (1 μm width and 25 μm length) are formed on a substrate. Cells are placed in the narrow grooves, and a culture solution is allowed to flow in the wide grooves to wash away and remove the unnecessary cells that are pushed out from the narrow grooves into the wide grooves as the cells proliferate. It is claimed that the cells in the narrow grooves can thus be cultured over many generations of 200 or more

RELATED ART REFERENCES

Non-patent Documents

Non-patent document 1: Wakamoto, Y. et al. (2001), Fres' J Anal Chem; Wakamoto, Y. et al. (2005), Analyst
Non-patent document 2: Current Biology, 22 Jun. 2010, Pages 1099-1103, "Robust Growth of *Escheruchia coli*", Ping Wang et al.

SUMMARY OF INVENTION

Problems that the Invention is to Solve

However, in the "mother machine", one end of the narrow whisker-like groove is closed, and it is thus designed such that the cells remaining in the narrow grooves are always old cells (mother cells) when the unnecessary cells are continuously removed. That is, in the "mother machine", there is no idea to eliminate the changes of physiological state associated with aging of the cultured cells remaining in the narrow whisker-like groove, and the "mother machine" has a problem that the changes of cellular physiological state associated with aging are inevitable.

Furthermore, in the "mother machine", the culturing environment around cells in the narrow groove is controlled by exchange of the culture solution through diffusion from the wide groove. In this method, when the narrow groove is long, there is a problem that the environmental conditions considerably vary between the region closer to the wide groove and the region far from the wide groove. Accordingly, for example, when a response of cells to a drug is observed with this method, the response of the cultured cell could be different simply due to the difference in the environmental condition, and an accurate verification of cellular response could be difficult.

The present invention was made in view of the above circumstances, and an object of the invention is to provide a cell culture apparatus, an apparatus for long-term observation of cell culture, a method for long-term cell culture and a method for long-term observation of cell culture, which are capable of continuously culturing and observing cells over long period of time under a uniform environmental condition without any variation in physiological state associated with aging of the cultured cells, and capable of tracing the history (genealogy) of a certain cell.

Means for Solving the Problems

The cell culture apparatus of the present invention is a cell culture apparatus comprising a cell culture substrate, a semipermeable membrane, and a culture solution supply means, for solving the above problems, wherein the cell culture substrate has, on the surface thereof, a narrow culture groove for holding and culturing cells and wide flow grooves for discarding the cells held and cultured in the culture groove, the both ends of the culture groove being connected to the flow grooves and the flow grooves being greater in width and depth than the culture groove; the semipermeable membrane is used so as to cover the culture groove and the flow grooves on the cell culture substrate; and the culture solution supply means is capable of continuously supplying culture solution to the cell culture substrate covered with the semipermeable membrane.

In the cell culture apparatus, it is preferred that the semipermeable membrane is capable of covering the cell culture substrate via biotin-avidin binding.

In the cell culture apparatus, it is more preferred that the culture solution supply means includes a liquid feeding pad.

The apparatus for long-term observation of cell culture of the present invention is characterized by comprising the above-mentioned cell culture apparatus and a microscope observation means capable of observing cells on the cell culture substrate.

In the apparatus for long-term observation of cell culture, it is preferred that an inverted microscope is used for microscopy.

The method for long-term cell culture of the present invention is a method for culturing cells over a long period of time by the above-mentioned cell culture apparatus. In addition, the method is characterized by comprising the steps of: holding desired cells in the culture groove of the cell culture substrate; covering the culture groove and the flow grooves of the cell culture substrate with the semipermeable membrane; and continuously feeding culture solution to the cell culture substrate by the supply means to supply the culture solution to the cells held in the culture groove of the cell culture substrate through the semipermeable membrane, while discarding a part of cells in the culture groove to the flow grooves by the culture solution flowing in the flow grooves connected to the both ends of the culture groove.

The method for long-term observation of cell culture of the present invention is a method for culturing and observing cells over a long period of time by the above-mentioned apparatus for long-term observation of cell culture. In addition, the method is characterized by comprising the steps of: holding desired cells in the culture groove of the cell culture substrate; covering the culture groove and the flow grooves of the cell culture substrate with the semipermeable membrane; continuously feeding culture solution to the cell culture substrate by the supply means to supply the culture solution to the cells held in the culture groove of the cell culture substrate through the semipermeable membrane, while discarding a part of cells in the culture groove to the flow grooves by the culture solution flowing in the flow grooves connected to the both ends of the culture groove; and observing the cells on the cell culture substrate by the microscope observation means.

Advantage of the Invention

According to the present invention, a long-term continuous culture becomes possible, and a growing state of cells can be observed over a long period of time while culturing the cells continuously under a uniform environmental condition or under an environmental condition with a regulated change, without involving any variation of the physiological state associated with aging of the cells to be cultured, and growth of a certain cell can be traced and observed over a long period of time. Accordingly, it becomes possible to measure a frequency distribution of cell size, a frequency distribution of growth rate, a frequency distribution of generation time, an autocorrelation function of expression level of a protein, and a cell genealogy.

MODE FOR CARRYING OUT THE INVENTION

Figure 1:
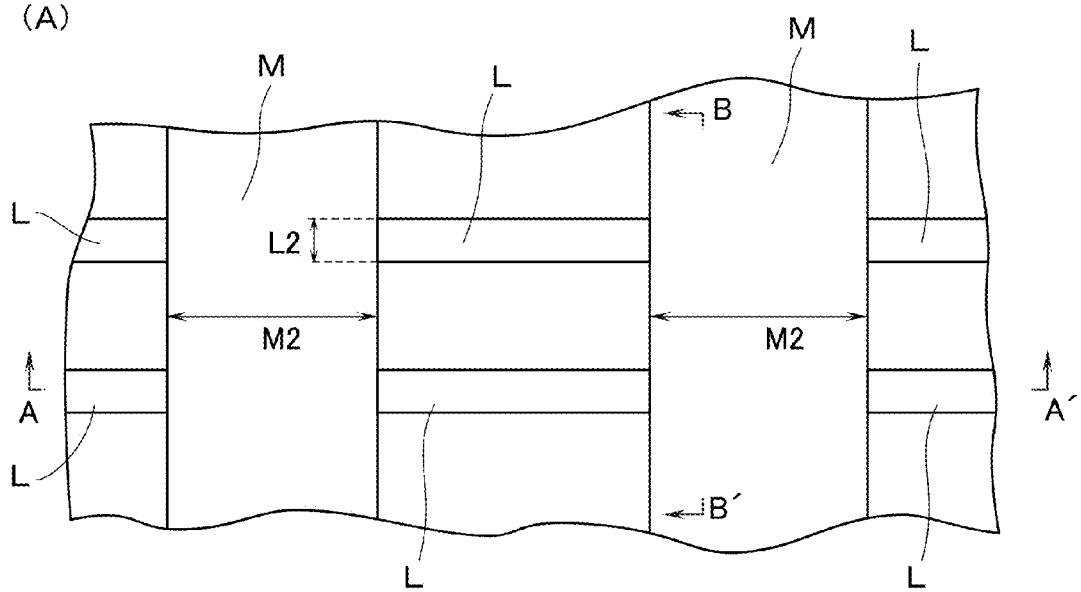
FIG. 1 (A) is a partially enlarged view illustrating one embodiment of the cell culture substrate constituting the cell culture apparatus of the present invention, (B) is a cross-section of FIG. 1(A) taken along line A-A', and (C) is a cross-section of FIG. 1(A) taken along line B-B'.
Figure 1:
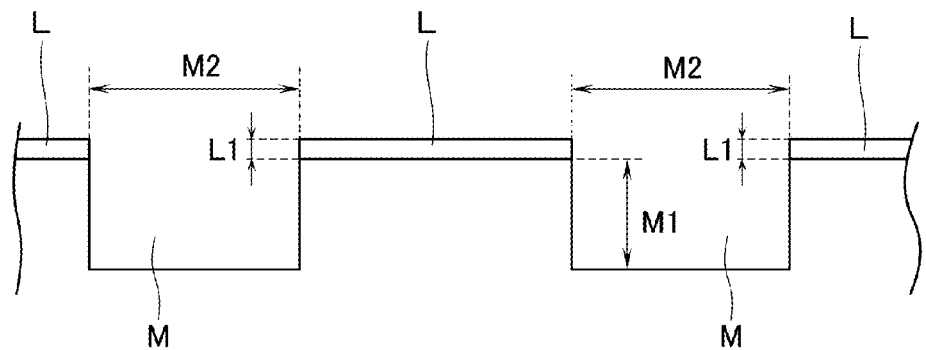
Figure 1:
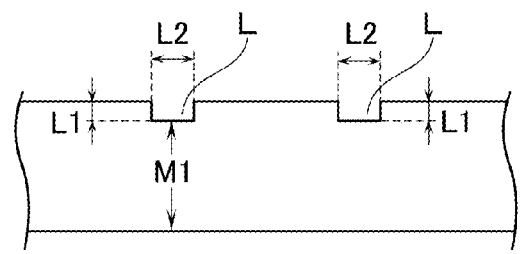

The cell culture apparatus of the present invention comprises a cell culture substrate, a semipermeable membrane, and a culture solution supply means.

FIG. 1(A) is a partially enlarged view illustrating one embodiment of the cell culture substrate constituting the cell culture apparatus of the invention. FIG. 1(B) is a cross-section of FIG. 1(A) taken along line A-A', and FIG. 1(C) is a cross section of FIG. 1(A) taken along line B-B'.

The cell culture substrate has a groove pattern formed on the surface thereof including narrow culture grooves L and wide flow grooves M in a lattice shape in which both ends of each narrow culture groove L are connected to the wide flow grooves M. The culture grooves L and the flow grooves M intersect each other at substantially right angles.

The culture grooves L serve as a region for holding cells in the grooves to enable continuous culture of the cells, and the flow grooves M serve as a region for moderately washing out and discarding the cells held and cultured in the culture grooves L, thereby regulating the environment in the culture grooves L.

In the present invention, the continuous culture means a cell culture over multiple generations, and in this invention, a long-term cell culture over many generations of 200 or more can be realized by controlling the environment around the cells.

The target cell of the present invention may be any cell types, and the type of the cell is not limited. Specifically, for example, a cell isolated from a human or nonhuman animal tissue, such as a stem cell, a skin cell, a mucosal cell, a liver cell, an islet cell, a nerve cell, a cartilage cell, an endothelial cell, an epithelial cell, a bone cell, a muscle cell, etc. and a plant cell, an insect cell, and a bacterial cell such as *E. coli* are included, and one or two or more of these cells may be cultured.

The culture grooves L are for holding cells therein, and therefore there is an assumption that the depth L1 and the width L2 of the groove are larger than the size of the cells to be cultured. Specifically, the groove depth L1 of the culture groove L may be designed to be 1 to 2 times, preferably 1 to 1.5 times as large as the cell size. The groove width L2 of the culture groove L may be designed to be 1 to 3 times, preferably 1 to 2 times as large as the cell size.

Here, "the cell size" is based on the diameter (the largest length) of the cell if the cell has a substantially spherical shape. If the cell has a shape other than a spherical shape, such as an elongated rod shape, the cell size may be determined based on the thickness (width) of the cell in a state where the cell is placed on a substrate, and in this case, the culture groove L may be designed such that the groove depth L1 is 1 to 2 times as large as the thickness (width) of the cell, and the groove width L2 is 1 to 3 times as large as the thickness (width) of the cell.

The cell size may be determined with reference to the known size described in literatures, or may be determined based on a result of an actual measurement of the cell size by means of a microscope or the like.

When the groove depth L1 and the groove depth L2 of the culture groove L are within the above range, cells can be held stably in the culture groove L, thereby making it possible to continuously culture and observe the cells. When the groove depth L1 of the culture groove L is more than twice as large as the cell size, it could occur that cells do not stay in the culture groove L and flow out to the flow grooves M, and it is difficult to hold and continuously culture the cells in the culture groove L. If the groove width L2 of the culture groove L is more than 3 times as large as the cell size, it could occur that the semipermeable membrane adheres to the interior of the culture groove to crush cells or prevent cells from flowing out to the flow grooves, and it is difficult to continuously culture the cells.

Meanwhile, the length of the culture groove L may be appropriately designed depending on the cell size, the number of the cells to be held and cultured in the culture groove L, or the like. Specifically, the length in the range of from 10 µm to 100 µm, preferably from 30 µm to 100 µm may be exemplified.

On the other hand, the flow groove M is formed to be wider and deeper than the culture groove L. That is, the groove depth M1 and the groove width M2 of the flow groove M are made larger than the groove depth L1 and the groove width L2 of the culture groove L. Here, "the groove depth M1 of the flow groove M" means a distance from the height of the bottom of the culture groove L to the bottom of the flow groove M, as shown in FIG. 1.

The groove depth M1 and the groove width M2 of the flow groove M may be appropriately designed in a range where cells in the culture groove L can be washed out, depending on the size and number of the cells to be held and cultured in the culture groove L and the flow rate of the cell culture solution running on the cell culture substrate. As a rough indication, the groove depth M1 of the flow groove M is preferably 3 to 50 times as large as the cell size. In relation to the culture groove L, a depth of 1.5 to 50 times as large as the groove L1 of the culture groove L may be exemplified. Specifically, a depth ranging from 5 µm to 50 µm may be preferably exemplified as the groove depth M1 of the flow groove M.

Furthermore, the groove width M2 of the flow groove M preferably has a size equal to or larger than the groove depth M1. In relation to the culture groove L, the length of 10 to 100 times as large as the groove width L2 of the culture groove L may be exemplified, and specifically the range of 10 µm or more, preferably 30 µm or more may be exemplified.

Thus, the groove depths (L1 and M1) and the groove width (L2 and M2) of the culture groove L and the flow groove M may be appropriately designed depending on the size of the desired cells to be cultured. As a specific example, it is known that *E. coli*, for example, has a size of 0.5 µm to 1.0 µm (width)×1.5 µm to 7.0 µm (length). In the case of continuously culturing *E. coli* by the cell culture apparatus of the invention, for example, a groove depth L1 ranging from 1.0 µm to 1.5 µm and a groove width L2 ranging from 1.0 µm to 3.0 µm as the size of the culture groove L of the cell culture substrate, and a groove depth M1 ranging from 5 µm to 20 µm and a groove width M2 ranging from 20 µm to 100 µm as the size of the flow groove M thereof, may be preferably exemplified.

As the material for the cell culture substrate, for example, glasses such as borosilicate grass and quartz glass, resins or plastics such as polystyrene, or silicon substrates are exemplified. Among them, a glass substrate is preferred since it is excellent in processability and handling property.

When producing the cell culture substrate with a glass, the culture grooves L and the flow grooves M can be formed on one surface of the glass plate to produce the cell culture substrate, for example, by patterning the shapes of the culture grooves L and the flow grooves M on photoresist through photolithography, and etching the substrate surface by a known method. Furthermore, the glass substrate may be appropriately subjected to a laser process or the like. As the patterning method other than photolithography, an electron beam direct drawing method and the like may be used. The surface of the cell culture substrate may be treated with a surface treating agent, or may be subjected to a physical surface processing treatment. For example, the surface of the cell culture substrate or a part thereof may be treated such that a function such as hydrophilicity, hydrophobicity and water repellency is imparted thereto. Examples of the treatment include a silicon coating, a functional group coating, in which a functional group such as an amino group, an isocyanate group, an epoxy group, a carboxy group, a hydroxy group, an SH group, a silanol group, etc. can be imparted to the surface. Preferred is a substrate having a surface modified with any of biotin, avidin, streptavidin, etc. Alternatively, the surface of the cell culture substrate may be coated with a cell adhesive matrix such as collagen, fibronectin, or gelatin.

Figure 2:
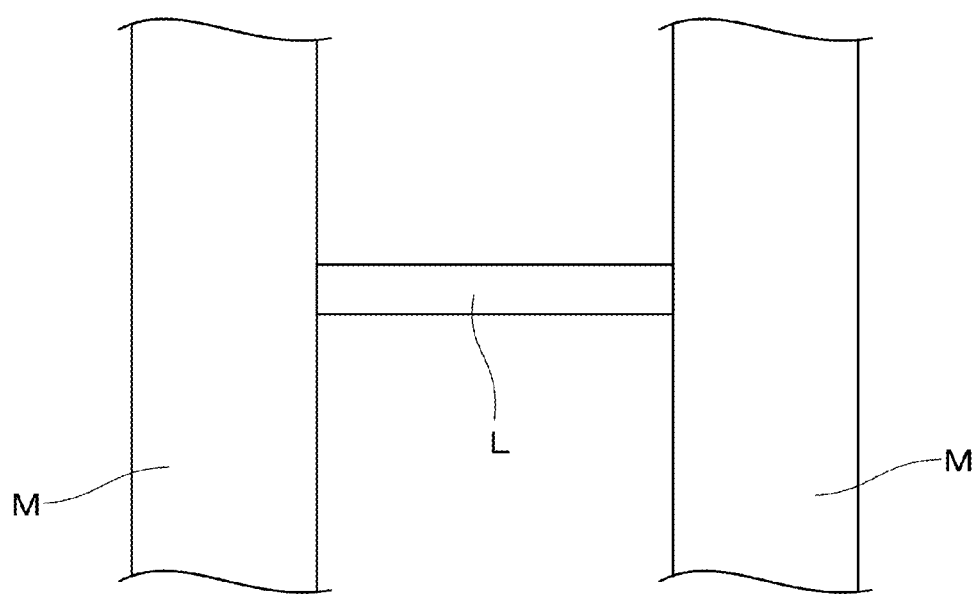
FIG. 2 It is a partially enlarged view illustrating another embodiment of the cell culture substrate constituting the cell culture apparatus of the present invention.

The groove pattern of the culture grooves L and the flow grooves M is not limited to the shape illustrated in FIG. 1. The cell culture substrate may have any configuration as long as the culture grooves L and the flow grooves M are connected at substantially right angles, and may have a configuration with a groove pattern in which one culture groove L is formed between two flow grooves M, as illustrated in FIG. 2. In addition, the flow grooves M need not necessarily be connected to the culture grooves L at precisely right angles as long as cells in the culture groove L can be appropriately washed out. Specifically, the angle of the flow groove M relative to the culture groove L may be allowed in a range around 90°±15°. In addition, the culture groove L and the flow groove M are preferably a straight line shape, but a curved section may be partially included. In FIG. 1, the cross sections of the culture grooves L and the flow grooves M are formed in a square shape, it is not limited to this shape, and may be such a shape that a bottom portion of the groove is curved.

The semipermeable membrane included in the cell culture apparatus of the present invention is used so as to cover the culture grooves and the flow grooves of the cell culture substrate. Examples of the semipermeable membrane which can be employed include a known one such as cellulose membrane. The semipermeable membrane is preferably modified with any of biotin, avidin, and streptavidin, and in this case, also in the cell culture substrate, it is preferred that the surface of the substrate is modified with any of biotin, avidin, and streptavidin. When the cell culture substrate is modified with biotin, a semipermeable membrane modified with avidin or streptavidin is used, and when the cell culture substrate is modified with avidin or streptavidin, a semipermeable membrane modified with biotin is used, thereby making it possible to seal the culture grooves L and the flow grooves M of the cell culture substrate from above via biotin-avidin binding. The semipermeable membrane makes it possible to consistently supply fresh culture solution to the cells from above.

When covering the upper surface of the cell culture substrate with the semipermeable membrane, the following methods can be exemplified, for example. At first, a thin film of a material that can undergo silane coupling with a silanol group, such as silicon or silicon oxides, chromium, aluminum, iron, or titanium, is vapor deposited or sputtered on the upper surface of the cell culture substrate. Then, an amino group, a carboxy group or an SH group is introduced to the surface of the thin film, for example, by a divalent regent having a silanol group at one end and an amino group, a carboxy group or an SH group at the other end, and biotin is covalently bound thereto. A semipermeable membrane such as cellulose membrane is modified with avidin or streptavidin, and the semipermeable membrane and the thin film are brought into contact with each other and connected via biotin-avidin binding, thereby being able to seal the upper surface of the cell culture substrate. Alternatively, it is also possible that the surface of the thin film on the cell culture substrate is bound to avidin or streptavidin, and the semipermeable membrane is bound to biotin. Incidentally, the semipermeable membrane is not necessarily limited to a configuration utilizing the biotin-avidin binding as long as the membrane can cover the flow grooves and the culture grooves of the cell culture substrate from above with a good adhesiveness.

One embodiment of the cell culture apparatus of the present invention will be explained below. FIG. 3(A) is a general view illustrating one embodiment of the cell culture apparatus of the invention, with a part shown in cross section. FIG. 3(B) is a schematic diagram illustrating a method of using the semipermeable membrane. Furthermore, FIG. 4 are pattern diagrams illustrating a state of cells when culture solution is supplied to the cell culture substrate covered with the semipermeable membrane, in which (A) is a plane view and (B) is a cross section.

The cell culture apparatus 1 comprises a cell culture substrate 2, a semipermeable membrane 3, and a culture solution supply means 4.

As described above, the cell culture substrate 2 has culture grooves L and flow grooves M formed thereon, and the upper surfaces thereof are covered with the semipermeable membrane 3. As illustrated in FIG. 3(B), the semipermeable membrane 3 may cover at least the area above the culture grooves L. When the both end sides of the flow grooves M are opened without covered with the semipermeable membrane 3, the culture solution can be supplied from one end of the flow groove M and discarded from the other end thereof. Meanwhile, cells are held in the culture grooves L covered with the semipermeable membrane 3.

A frame seal S is provided on the surface of the cell culture substrate 2 around the culture grooves L and the flow grooves M. As the frame seal, a material which has an appropriate thickness and has an adhesive property on its front and rear surfaces may be preferably exemplified, but the frame seal is not particularly restricted.

The culture solution supply means 4 includes a liquid feeding pump 41 (a syringe), a liquid feeding pad 42, and a waste liquid tank 43.

The liquid feeding pump 41 is connected to a through hole at one end of the liquid feeding pad 42 via a liquid feeding tube, and is capable of pumping culture liquid for cells and supplying the culture liquid to the cell culture substrate 2.

The liquid feeding pad 42 is disposed on the cell culture substrate 2 to cover the culture grooves L, the flow grooves M and the semipermeable membrane 3 so as to be adhered and sealed on the periphery of an area containing the culture grooves L, the flow grooves M and the semipermeable membrane 3 via the frame seal S. Meanwhile, the liquid feeding pad 42 is provided with at least one through hole at one end thereof through which the culture solution flows in and at least one through hole at the other end thereof through which the waste culture solution is discarded out such that the through holes pass through the pad surface. These through holes may be disposed such that the culture solution flows from the thorough hole for flowing in of the culture solution to the through hole for discarding out thereof in a space that is formed between the liquid feeding pad 42 and the cell culture substrate 2 and filled with the culture solution.

That is, the liquid feeding pad 42 has a function for consistently holding fresh culture solution on the cell culture substrate 2.

The liquid feeding pad 42 can be obtained using a hard material such as glass and acrylic or a soft material such as rubber and elastomer, with no particular restriction. With respect to the transparency of the liquid feeding pad 42, although a transparent material is suitable when transmitted light from the upper surface of the cell culture apparatus 1 is required for microscope observation, the liquid feeding pad 42 is not necessarily transparent when transmitted light is not required, such as in a fluorescent observation.

In this embodiment, the liquid feeding pad 42 is adhered on the upper side of the cell culture substrate 2 via the frame seal S, as shown in FIG. 3(A). A space is formed between the cell culture substrate 2 and the liquid feeding pad 42, and the space is filled with the culture solution supplied from the liquid feeding pump during the culturing. The culture solution passing on the cell culture substrate 2 is then fed out to the waste liquid tank 43 connected to the liquid feeding pad 42 at the above-mentioned through hole of the liquid feeding pad 42. As the liquid feeding pad 42, a transparent pad formed of polydimethylsiloxane (PDMS) may be preferably exemplified. The liquid feeding pad 42 of PDMS may be formed in a box-and-lid shape by applying a photoresist on a silicon wafer to produce a convex mold with an inverted groove with lithography, pouring PDMS resin into the mold, and heating it to mold the resin. In addition, the liquid feeding pad 42 may be provided with, for example, a foam trapping groove or the like for removing foams in the culture solution in the interior bottom of the box-and-lid.

In FIG. 3(A), the culture solution supply means 4 is disposed such that the supply direction of the culture solution supplied from the liquid feeding pump 41 to the cell culture substrate 2 coincides with the longitudinal direction of the flow grooves M of the cell culture substrate 2.

Figure 6:
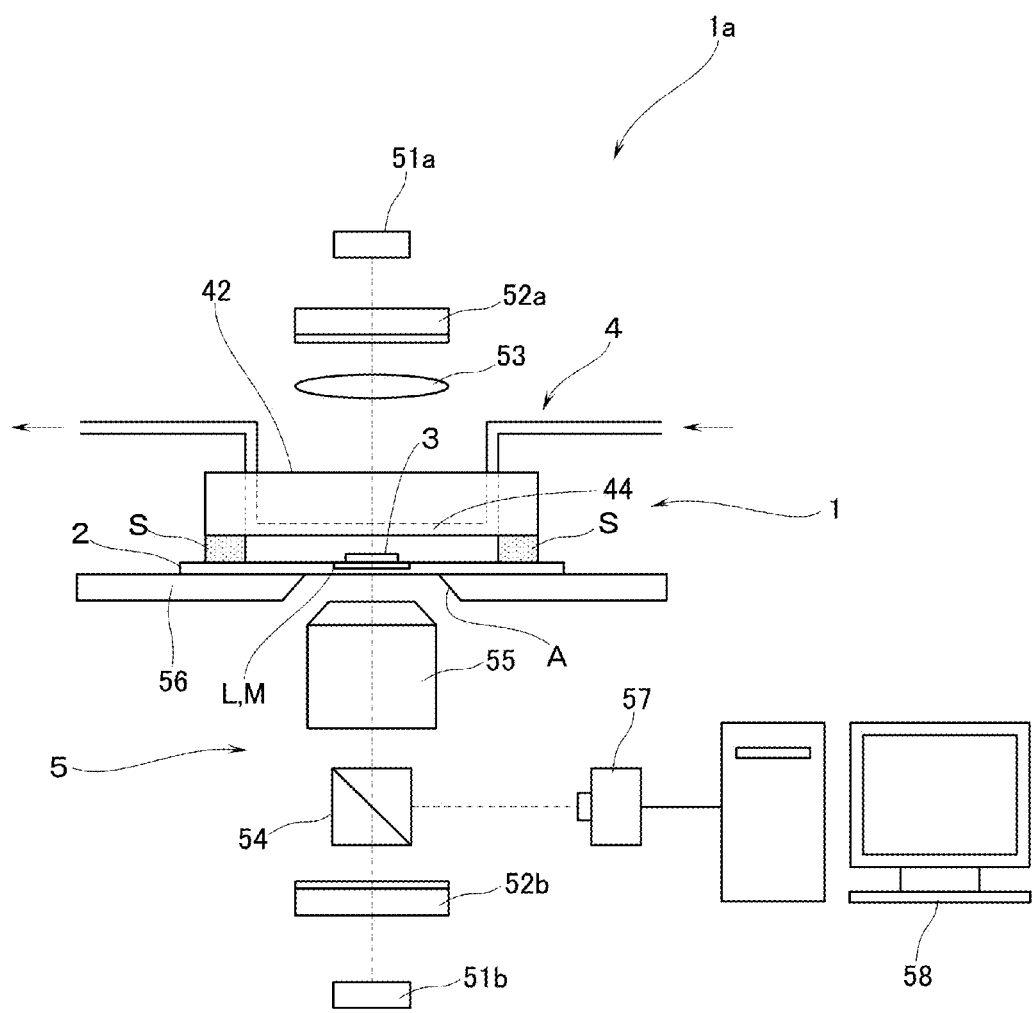
FIG. 6 It is a general view illustrating one embodiment of the apparatus for long-term observation of cell culture of the present invention, with one part shown in cross section.

Further as shown in FIG. 6, the cell culture apparatus 1 of the present invention may be configured to include an apparatus for long-term observation of cell culture along with a microscope observation means 5 capable of observing cells on the cell culture substrate 2. Examples of the microscope observation means 5 may include an apparatus provided with an optical system such as a lens for enlarging an image of cells to be observed, and specifically, an inverted microscope, an optical microscope, a fluorescence microscope, a video recorder, and a camera may be exemplified. These microscope observation means may be connected to a personal computer or the like to process the image, and may also be used along with a photoirradiation apparatus for facilitating the cell observation.

Next, one embodiment of the method for long-term cell culture and the method for long-term observation of cell culture, utilizing the cell culture apparatus of the present invention will be explained.

Figure 3:
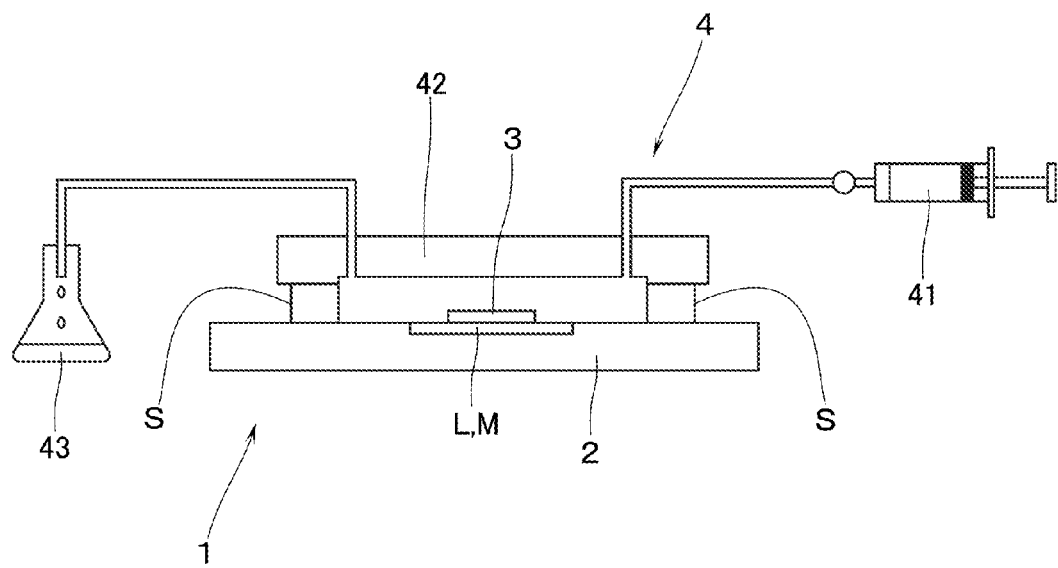
FIG. 3 (A) is a general view illustrating one embodiment of the cell culture apparatus of the present invention with one part shown in cross-section, and (B) is a schematic diagram illustrating a method for using the semipermeable membrane.
Figure 3:
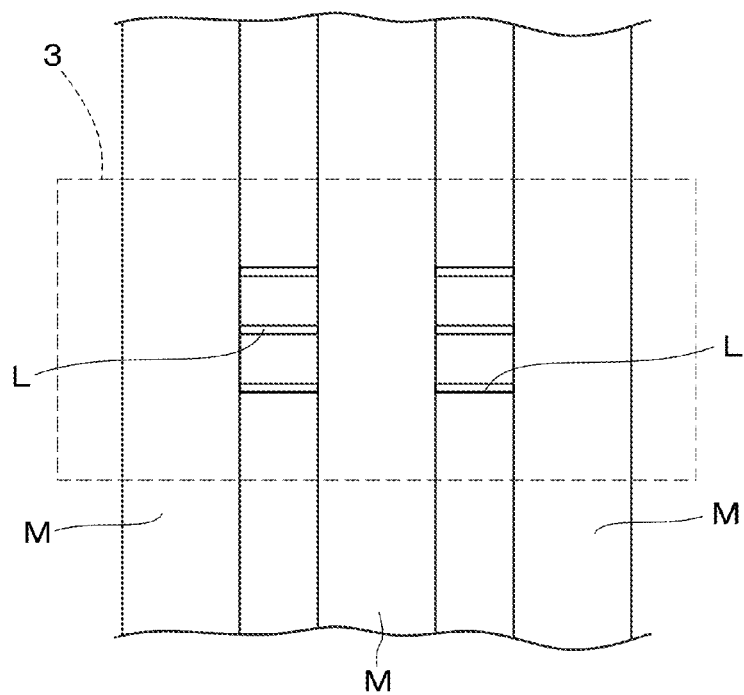
Figure 4:
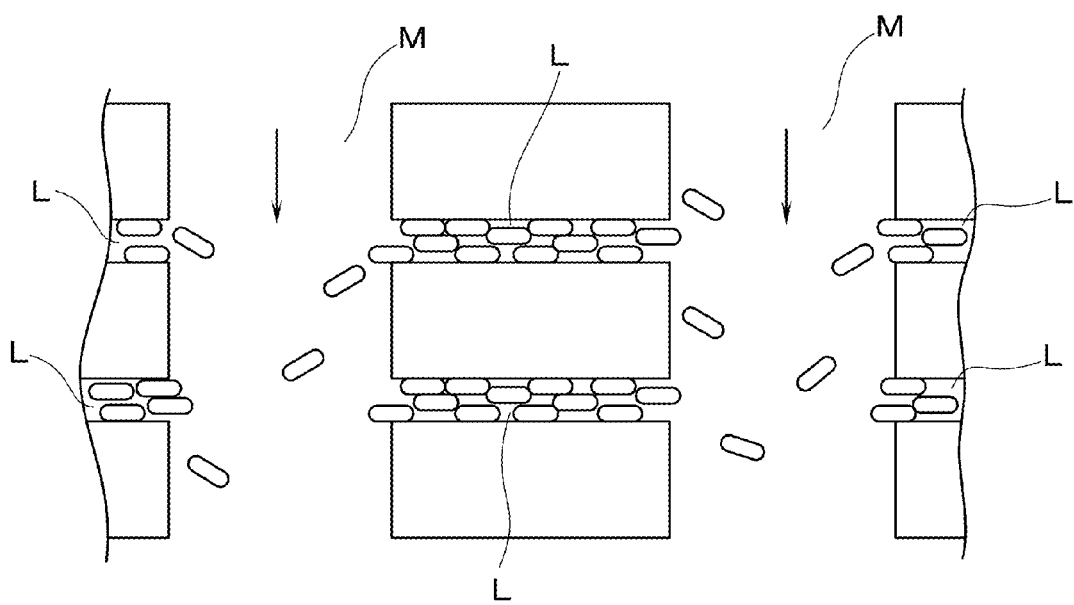
FIG. 4 They are pattern diagrams illustrating a state of cells when supplying culture solution to the cell culture substrate covered with the semipermeable membrane, in which (A) is a plane view, and (B) is a cross-sectional view.
Figure 4:
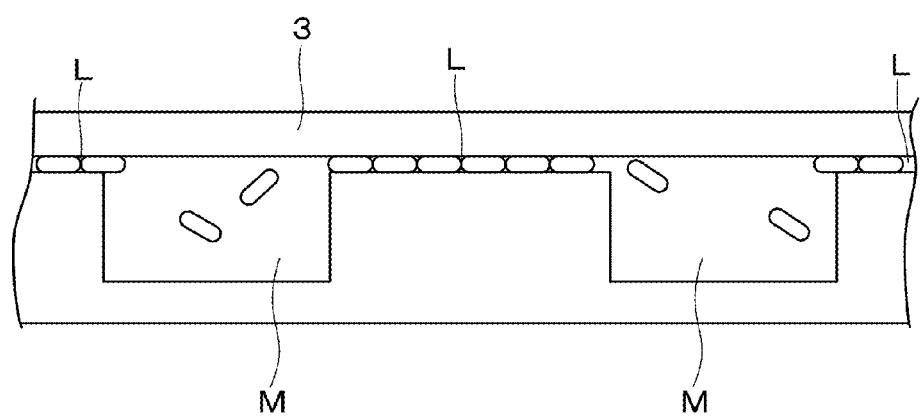
Figure 5:
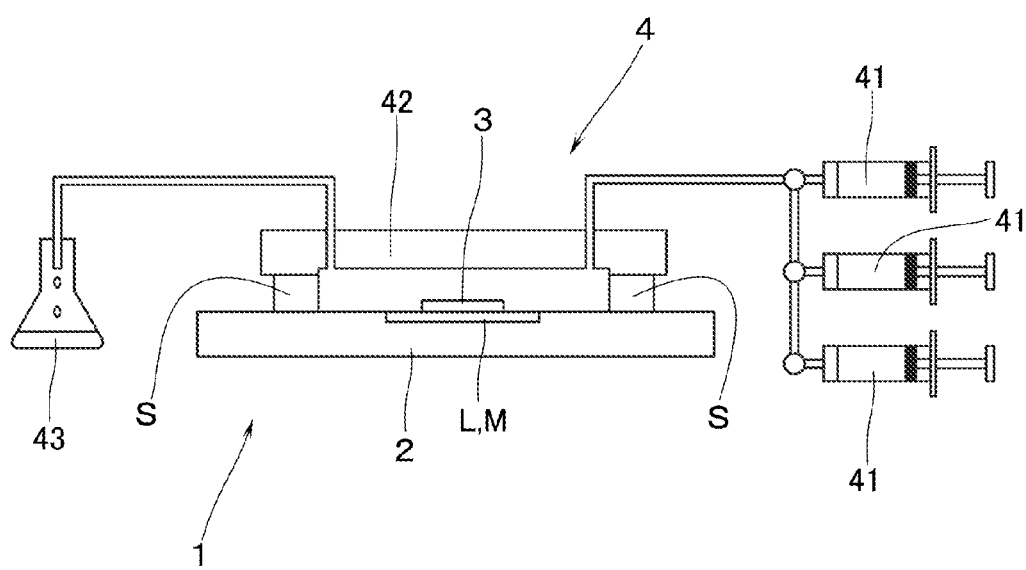
FIG. 5 It is a general view illustrating another embodiment of the cell culture apparatus of the present invention, with one part shown in cross section.

The liquid feeding pump 41 of the supply means 4 in FIGS. 3 and 5 is driven to feed culture solution onto the cell culture substrate 2. Since the direction of liquid feeding of the culture solution from the liquid feeding pump 41 to the cell culture substrate 2 coincides with the direction of the flow grooves M of the cell culture substrate 2, the culture solution supplied from the liquid feeding pump 41 is smoothly flown in from one end of the flow grooves M and passes on the cell culture substrate 2 while filling the interior space between the liquid feeding pad 42 and the cell culture substrate 2. For example, the culture solution may be fed at a feeding rate ranging approximately from 0.5 ml/hr to 200 ml/hr.

Since the upper surface of the cell culture substrate 2 is covered with the semipermeable membrane 3 at this time, when the culture solution is allowed to flow on the cell culture substrate 2, the culture solution can be supplied while suppressing the outflow of the cells held and cultured in the culture grooves L. Since wide flow grooves M are connected to both ends of a narrow culture groove L in the cell culture substrate 2, for example, there may be a case where the flow rates of culture solution running in the opposite two flow grooves M are slightly different from each other. Thus, when the semipermeable membrane 3 is not used, the culture solution may flow into the culture groove L at a high speed and cells could be flushed out from the culture groove L to the flow groove M. By covering the culture grooves L of the cell culture substrate 2 with the semipermeable membrane 3, it is suppressed that the culture solution flows from the flow grooves M into the culture grooves L and it is possible to stably hold the cells in the culture grooves L.

Furthermore, the culture solution is supplied to the cells held in the culture grooves L by permeation and diffusion of the culture solution flowing on the upper side of the semipermeable membrane 3, through the semipermeable membrane 3. Thus, for example, when the culture grooves L are formed with a large length of 30 μm or more, a stable and uniform environmental condition is maintained in the culture grooves L. Also, the uniformity of the culture environment makes it possible to precisely verify the response of cells to drugs or the like.

FIG. 4 are pattern diagrams illustrating a state of cells when culture solution is supplied to the cell culture substrate covered with the semipermeable membrane. In FIG. 4, the illustration of the boundary lines of the connection parts of the culture grooves L and the flow grooves M is omitted. FIG. 4(A) is a plane view and FIG. 4(B) is a cross section.

By the supply of the culture solution through the semipermeable membrane 3, the cells in the culture grooves L can be stably cultured and proliferate exponentially. Once the cells fill the interior of each culture groove L, a part of the cells located near the both ends of the culture groove L (near the connection parts of the flow grooves M and the culture groove L) is washed out, by the culture solution flowing in the flow grooves M connected to the both ends of the culture groove L at a substantially right angle, into the flow grooves M, and discarded with the culture solution and collected in the waste liquid tank 43. Accordingly, the number of the cells in the culture groove L can be maintained in a prescribed number such that the problems of the nutrient consumption of cells, accumulation of waste products, variation of environment around cells, and the like, which conventionally have arisen with the lapse of time, can be eliminated. With the apparatus for long-term observation of cell culture using the microscope observation means 5, it is possible to continuously culture and observe cells over many generations as large as 200 or more. This also makes it possible to measure information including a growth rate, a magnitude of fluctuation in a gene expression, and an autocorrelation function, in one cell line, based on the time series data over an unprecedentedly long period of time. Since the time period over 100 or more generations corresponds to a time scale where an evolution event involving a change in the genetic type occurs, the cell culture apparatus and the apparatus for long-term observation of cell culture of the present invention can be applied to the evolution study which has been difficult to demonstrate and verify experimentally.

In addition, in the cell culture substrate constituting the cell culture apparatus of the present invention, the flow grooves M are connected to both ends of a culture groove L, and therefore cells in the culture grooves L have flowability such that the stay of the mother cells in the culture grooves L as seen in the conventional "mother machine" can be avoided. Accordingly, it can be suppressed that the cells in the culture grooves L involve the variation in physiological state associated with aging.

Since the cells remaining in the culture grooves L are those resulting from the division of the cells which have existed in the culture grooves L (mother cells), a history (genealogy) of a certain cell can be traced and can be observed and analyzed by the apparatus for long-term observation of cell culture, through image analysis, etc. with the microscope observation means 5 and a computer.

Furthermore, the cell culture apparatus and the apparatus for long-term observation of cell culture of the present invention can be used for detecting a gene mutation. Specifically, this is possible using a cell line that is designed such that, when a gene mutation such as frame shift mutation and point mutation occurs at a certain site, a fluorescent protein located at the site is expressed in the correct sequence. When the mutation occurs in a cell present in the culture groove, the cell starts to emit fluorescence due to the expression of the fluorescent protein, thereby making it possible to detect the occurrence of the mutation without killing the cell. This cell is continuously observed over a long-term in the cell culture apparatus, whereby the information such as the frequency of occurrence of the gene mutation, the timing of the occurrence during the division cycle, and the like can be obtained.

FIG. 5 is a general view illustrating another embodiment of the cell culture apparatus of the present invention, with one part shown in cross section. The explanation of the parts in common with the embodiment shown in FIGS. 3 and 4 will be omitted here.

In the cell culture apparatus 1 illustrated in FIG. 5, a plurality of liquid feeding pumps 41 are connected to a liquid feeding pad 42, and culture solution can be supplied from each of the liquid feeding pump to a cell culture substrate 2 covered with a semipermeable membrane 3. In this embodiment, for example, different culture solutions containing different components are placed in the respective liquid feeding pumps 41 and the liquid feeding pump to be used is switched at an appropriate timing during the continuous culture. It is thus possible to provide various changes in environmental condition to the cells held in the culture grooves L of the cell culture substrate 2, and to verify the effect of the change of the environmental condition on the cells over a long period of time.

FIG. 6 is a general view illustrating one embodiment of the apparatus for long-term observation of cell culture of the present invention, with one part shown in cross section. The explanation of the parts in common with the embodiment shown with FIGS. 3 and 5 will be omitted here.

The apparatus for long-term observation of cell culture 1a illustrated in FIG. 6 includes a cell culture apparatus 1 and a microscope observation means 5.

In this embodiment, an inverted electric microscope having a function of fluorescent microscope is used as the microscope observation means 5 suitable for the temporal observation of a growth rate of a cell, an expression of a fluorescent protein and the like, as described above.

The inverted electric microscope (microscope observation means 5) includes a bright field observation light source 51a, fluorescent observation light source 51b, an automatic shutter 52a, an automatic shutter 52b, a condenser lens 53, a dichroic mirror 54, an objective lens 55, and an XY stage 56. The XY stage 56 has an opening A, and the cell culture substrate 2 of the cell culture apparatus 1 is placed on the XY stage 56 such that the culture grooves L in which cells are held is positioned in the opening A.

Cells held in the culture grooves L can be moved to a position where the observation is desired to be made, automatically by the XY stage 56 driven with an electric motor. The objective lens 55 is adjacently disposed below the opening A of the XY stage 56. The XY stage 56 is separately moved in the X-Y axis direction across the optical axis and the objective lens 55 is moved in a vertical direction of 2 axis, whereby the relative position of the XY stage 56 and the objective lens 55 can be adjusted. Also, the relative distance of the XY stage 56 to the objective lens 55 can be adjusted by moving the XY stage 56 in a 2 axis direction independently, in addition to the X-Y axis direction.

The inverted electric microscope includes a bright field transmitted illumination system, an epi-illumination system, and an imaging system, inside a main body case not shown. The bright field transmitted illumination system is disposed above the height of the XY stage 56, and the epi-illumination system and the imaging system are disposed below the height of the XY stage 56.

The bright field transmitted illumination system is used for an observation with a transmitted light. The bright field transmitted illumination system includes a bright field observation light source 51a, an automatic shutter 52a, and a condenser lens 53. As the bright field observation light source 51a, a halogen lamp and the like may be used. The light emitted from the bright field observation light source 51a passes through the condenser lens 53 in a state where the automatic shutter 52a is opened, and irradiates cells held in the culture grooves L of the cell culture substrate 2 placed on the XY stage 56, downwardly in the vertical direction.

The epi-illumination system is used for an observation with fluorescence. The epi-illumination system includes a fluorescent observation light source 51b, an automatic shutter 52b, and a dichroic mirror 54. As the fluorescent observation light source 51b, a mercury lamp or the like may be used. The epi-illumination system may further includes an optical system such as a heat absorption filter, a collector lens, and an excitation filter for making the light from the fluorescent observation light source 51b into excitation light having a specific short wavelength band. The light emitted from the fluorescent observation light source 51b passes through the dichroic mirror 54 and the objective lens 55 in a state where the automatic shutter 52b is opened, and irradiates cells held in the culture grooves L of the cell culture substrate 2 placed on the XY stage 56, from the opening A upwardly in the vertical direction.

The imaging system includes a camera 57 mounted facing the dichroic mirror 54. As the camera 57, for example, a CCD camera may be used.

The inverted electric microscope is further provided with a power source unit and a motor driving circuit board. The power source unit includes a power source for the bright field observation light source 51a, a power source for controlling a system, such as a motor, incorporated into the inverted electric microscope, a power source for the fluorescent observation light source 51b, etc. The motor driving circuit board controls, for example, a motor for driving the XY stage 56 in an X-Y axis direction, a motor for driving an electric zoom mechanism for the imaging system, a motor for driving a diaphragm for the fluorescent observation light source 51b such as a mercury lamp, etc.

Various operations and settings of the inverted electric microscope can be made by a user through a computer 58 such as a personal computer, using a keyboard or a mouse.

The transmitted illumination system and the epi-illumination system are selectively used. When the transmitted illumination system is selected, an image of the cells held in the culture grooves L obtained by transmitted illumination light from the bright field observation light source 51a passes through the objective lens 55 from the opening A and reflected on the dichroic mirror 54, then being captured by the camera 57 disposed facing in the horizontal direction.

On the other hand, when the epi-illumination system is selected, an fluorescent image of cells held in the culture grooves L obtained by irradiation of excitation light from the fluorescent observation light source 51b passes through the objective lens 55 form the opening A and reflected on the dichroic mirror 54, then being captured by the camera 57 disposed facing in the horizontal direction.

Although not shown, the inverted electric microscope further includes an ocular lens for observing cells with eye and an optical system for optically connecting the ocular lens and the objective lens 55. This optical system includes a mirror, a relay lens, and an optical path switching prism. For example, in the case of observation with the camera 57, the optical path switching prism is inserted in the optical axis for the observation, the primary image from the objective lens can be reflected on the optical path switching prism, thereby being observed by the camera 57. On the other hand, in the case of observation with eye, the optical path switching prism is eliminated from the optical axis for the observation, and the objective lens primary image is reflected on the mirror toward the ocular lens. The objective lens primary image can be further relayed on the relay lens, thereby being observed with eye by the ocular lens.

Using the cell culture apparatus 1 of the configuration as described above, the following cell observation can be carried out.

In the same manner as in the embodiment of FIGS. 3 and 5, culture solution is supplied between the cell culture substrate 2 and the liquid feeding pad 42 which is adhered on the upper side of the cell culture substrate 2 via the frame seal S, by a culture solution supply means 4. In this embodiment, the liquid feeding pad 42 is provided with a foam trapping groove 44 which is a groove for removing foams in the culture solution, as described above.

In this embodiment, it is important that the position for observation of the microscope observation means 5 is made below the cell culture apparatus 1 by using an inverted electric microscope as the microscope observation means 5.

With such a location, foams in the culture solution supplied between the liquid feeding pad 42 and the cell culture substrate 2 are removed upward by the foam trapping groove 44 on the upper side of the cell culture substrate 2, and an enlarged image of the cells held in the culture grooves L can be obtained from the underside, i.e., the opposite side of the above, of the cell culture substrate 2, by the objective lens 55 through the opening A of the XY stage 56.

Thus, it is prevented that the foams generated in the cell culture apparatus 1 interferes with the observation by the microscope observation means 5, and a long-term continuous cell observation, for example, a long-term continuous cell observation for 200 generations, becomes possible.

Cells in the culture grooves L are stably cultured by supplying culture solution through the semipermeable membrane 3 and proliferated exponentially. Then, once the cells fill the culture grooves L, a part of the cells located near the both ends of a culture groove L is washed out into flow grooves M by the culture solution flowing in the flow grooves M connected to the both ends of the culture groove L at substantially right angles, and discarded with the culture solution.

The cells thus cultured in the culture grooves L can be observed with the camera 57 or the ocular lens as an image enlarged using the objective lens 55 by being irradiated with light of either of transmitted illumination system or epi-illumination system.

In the case of an observation by the transmitted illumination system, specifically, it is possible to observe a cell size as described above, in particular, the variation and the growth rate of the cell size in a certain cell line, and the like.

In a fluorescent observation by the epi-illumination system, specifically, it is possible to observe an expression level of a fluorescent protein inside a cell and the variation thereof, as described above, a fluorescent image of stained cells and the variation thereof, and the like.

That is, since the cells remaining in the culture grooves L are those resulting from the division of the cells which have existed in the culture grooves L (mother cells), a history of a certain cell can be traced and can be observed and analyzed, by image analysis with the microscope observation means 5 and a computer 58.

For example, a fluorescent image of a fluorescent protein or the like can be captured by the camera 57 with time and recorded in the computer 58, thereby performing a time-lapse measurement. This time-lapse image can be analyzed by the computer 58 using a dedicated software for image analysis, thereby obtaining time series information with respect to the cell size contained in the obtained image, the average of the interior fluorescence brightness, etc. This makes it possible to measure information including a growth rate, a magnitude of fluctuation in a gene expression, and an autocorrelation function, in one cell line, based on the time series data over an unprecedentedly long period of time.

The present invention is not to be limited to the above embodiments. Needless to say, many embodiments varied in details can be made.

EXAMPLES

The present invention will be explained in more detail below with reference to the Examples. The present invention is not, by no means, limited to the Examples.

Example 1

Production of Cell Culture Substrate

On a glass substrate (60 mm length×24 mm width×0.17 mm thickness), as a cell culture substrate for continuously culturing *E. coli*, 50 culture grooves L (groove depth L1: 1.0 µm, groove width L2: 3.0 µm and length: 30 µm) and 20 flow grooves M (groove depth M1: 17 µm, groove width M2: 60 µm and length: 5000 µm) were formed in a lattice shape (see FIG. 1).

Example 2

Coverage with Semipermeable Membrane

A surface of the cell culture substrate produced in Example 1 was modified with biotin. Meanwhile, a semipermeable membrane made of cellulose of 1 mm width×1 mm length was used as the semipermeable membrane, and the surface thereof is modified with streptavidin. Then, 1 µl of culture solution containing *E. coli* was dropped from above to the culture grooves L and the flow grooves M on the surface of the cell culture substrate, and thereafter, a part of the area of the central portion above the culture grooves L and the flow grooves M of the cell culture substrate was sealed with the semipermeable membrane.

Example 3

Culture and Observation of Cells

Cells were continuously cultured and observed by the cell culture apparatus of the present invention. Specifically, a frame seal (SLF-0201, manufactured by Bio-Rad) having a rectangular frame shape which was a double-sided tape was adhered on the cell culture substrate such that the frame seal surrounded the culture grooves and the flow grooves, and a PDMS liquid feeding pad was attached to the upper surface of the frame seal. One of two silicone tubes mounted to the PDMS liquid feeding pad was connected to a syringe (a liquid feeding pump) and another one was introduced into a waste liquid tank (see FIG. 3). Using the syringe, M9 minimal medium for *E. coli* culture containing 0.2% by weight of glucose as a nutrient was allowed to flow continuously at a flow rate of 2 ml/hr. The apparatus for long-term observation of cell culture as shown in FIG. 6 was configured by placing this cell culture apparatus on a stage of an inverted electric microscope, and a time-lapse observation of the cells in the culture grooves was performed at 2 minute intervals using a phase contrast objective lens of 100 times magnification.

Specifically, the *E. coli* used in the observation was W3110 strain containing a plasmid expressing a fluorescent protein (GFP) in a manner of being regulated by the promoter of rpsL gene.

In the time-lapse measurement, a GFP fluorescent image of the cell was obtained and recorded on a PC. This time-lapse image was analyzed using an image analysis software, ImageJ (http://rsbweb.nih.gov/ij/), thereby obtaining the time series information with respect to the size of cells contained in the obtained image and the average of the interior fluorescence brightness (corresponding to the intracellular concentration of GFP).

Figure 7:
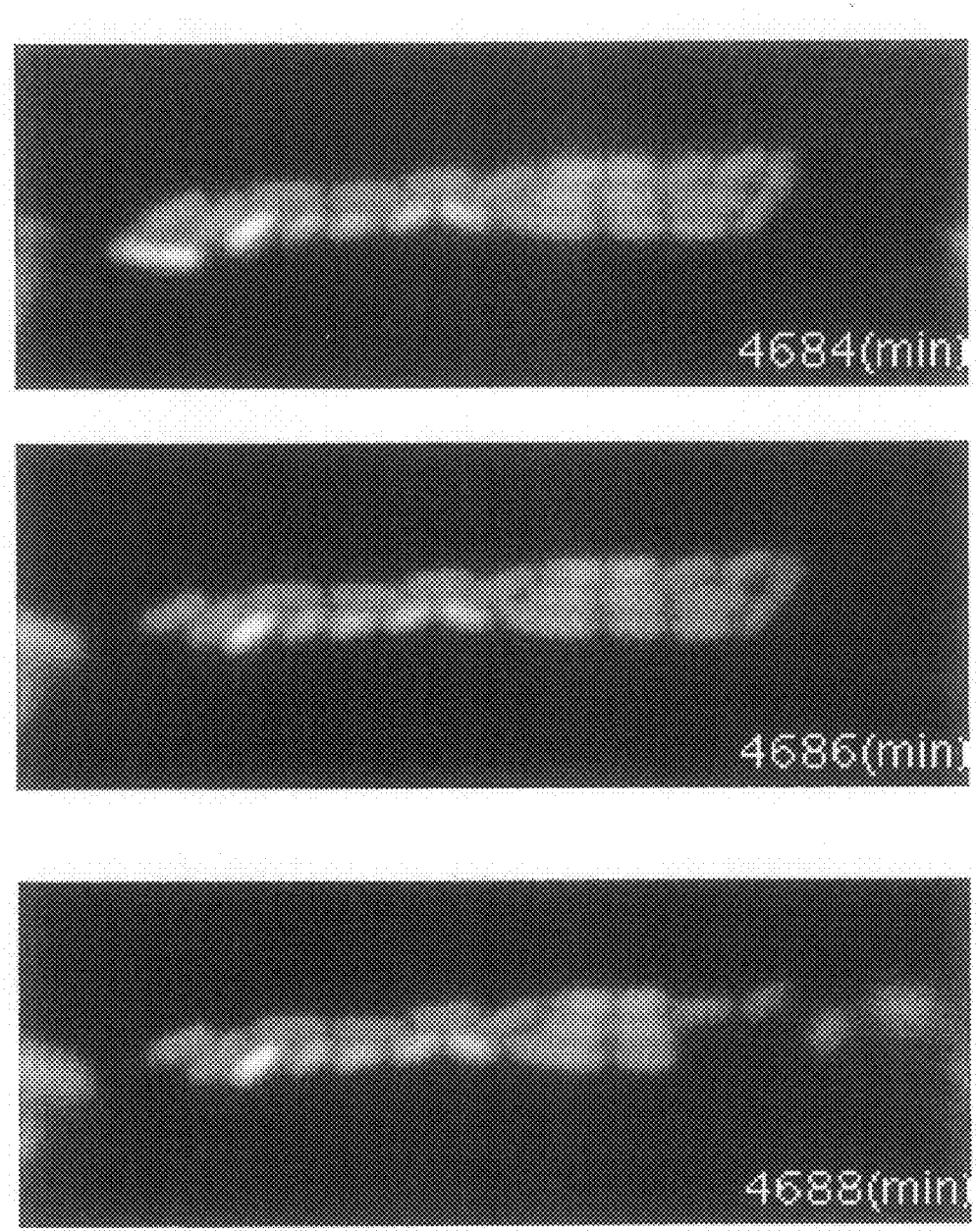
FIG. 7 It is a part of continuous images recording a state of cells present in a culture groove of the cell culture substrate.

FIG. 7 is a part of continuous images recording the state of the cells present in the culture grooves on the cell culture substrate.

As shown in FIG. 7, it can be confirmed that when cells are continuously cultured while supplying culture solution to the cell culture substrate, among the cells present in the culture groove, a part of cells present at the both ends of the culture groove is moderately washed out to the flow grooves and disappears from the picture. Also, it is confirmed that cells are held and cultured in the culture grooves L stably due to the groove shape of the cell culture substrate and the semipermeable membrane. In addition, a stable and uniform environment of the interior of the culture grooves L is maintained due to the supply of the culture solution to the cells through the semipermeable membrane.

It was confirmed that the number of the cells in the culture grooves L can be maintained to a prescribed number by the cells present at the both ends of the culture grooves being moderately washed out to the flow grooves, thereby solving the problems such as nutrient consumption by cells, accumulation of waste products, and variation of environment around the cells, which have conventionally occurred with the lapse of time, and thus enabling continuous culture and observation of the cells. It was also confirmed that the stay of the mother cells in the culture grooves L can be avoided, thereby enabling the long-term culture of cells in the culture grooves L without any variation of physiological state associated with aging.

Figure 8:
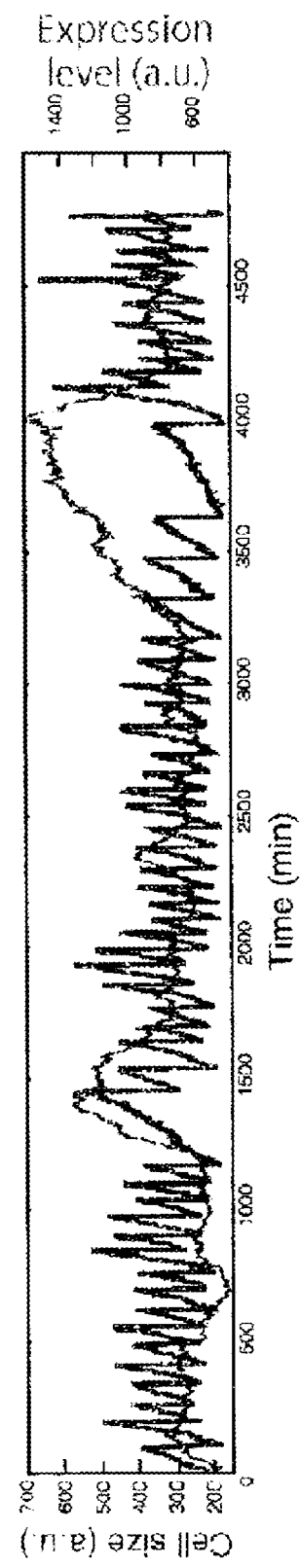
FIG. 8 A graph by plotting the variation of cell size and the variation of the GFP expression level in the cell (intracellular concentration), over 55 generations in one cell line, obtained by the image analysis.

FIG. 8 is a graph by plotting the variation of cell size and the variation of the GFP expression level in the cell (intracellular concentration), over 55 generations in one cell line, obtained by the image analysis.

As shown in FIG. 8, it was confirmed that a continuous cell culture over a long period of time is possible by the cell culture apparatus of the present invention. It was confirmed that it becomes possible with this apparatus to measure the information such as the growth rate (variation of cell size) and the magnitude of fluctuation in gene expression level, in one cell line, based on a time series data for an unprecedentedly long period of time.

Example 4

Frequency Distribution of Protein Expression Level

A cell culture apparatus including a cell culture substrate, a PDMS liquid feeding pad, a syringe (liquid feeding pump) and a waste liquid tank, similar as in Example 3, was placed on a stage of an inverted electric microscope, and a time-lapse observation was performed for *E. coli* expressing a fluorescent protein GFP in the culture grooves. With the syringe, M9 minimal medium for *E. coli* culture containing 0.2% by weight of glucose as nutrient was allowed to flow continuously at a flow rate of 2 ml/hr. The culture temperature during the observation was maintained at 37° C., and the time-lapse observation of the cells in the culture grooves was made at 1 minute intervals over 5000 minutes.

Figure 9:
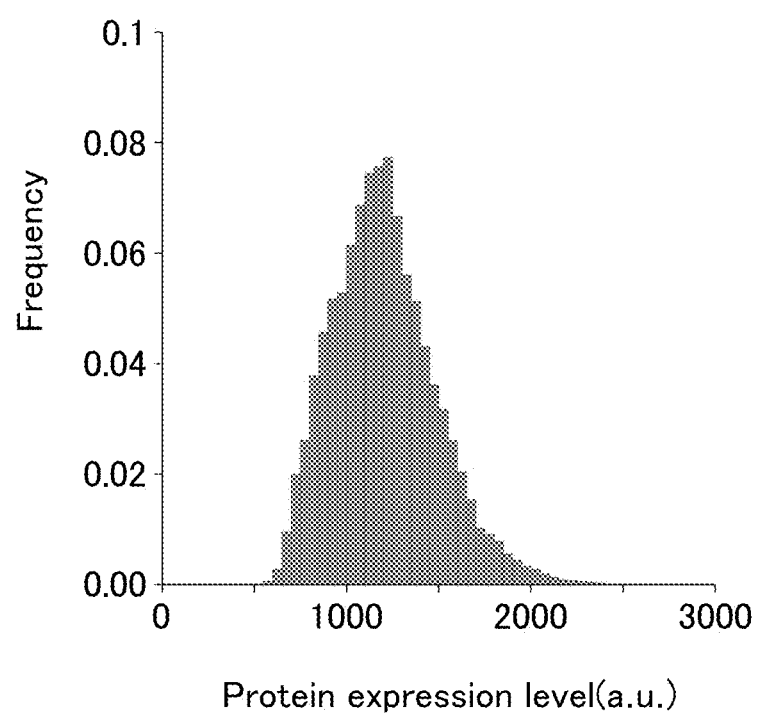
FIG. 9 It is a graph showing a result of measurement of a frequency distribution of GFP expression level, which was estimated based on a measurement in which a time-lapse observation was made for a GFP-expressing E. coli, to determine the intracellular GFP average fluorescence brightness of all the cells et all the observation time point (Example 4).

The intracellular GFP average fluorescence brightness of all the cells at all the observation time point was measured, and the frequency distribution of GFP expression level estimated based on this data was determined. The result is shown in FIG. 9.

Example 5

Frequency Distribution of Cell Size

Figure 10:
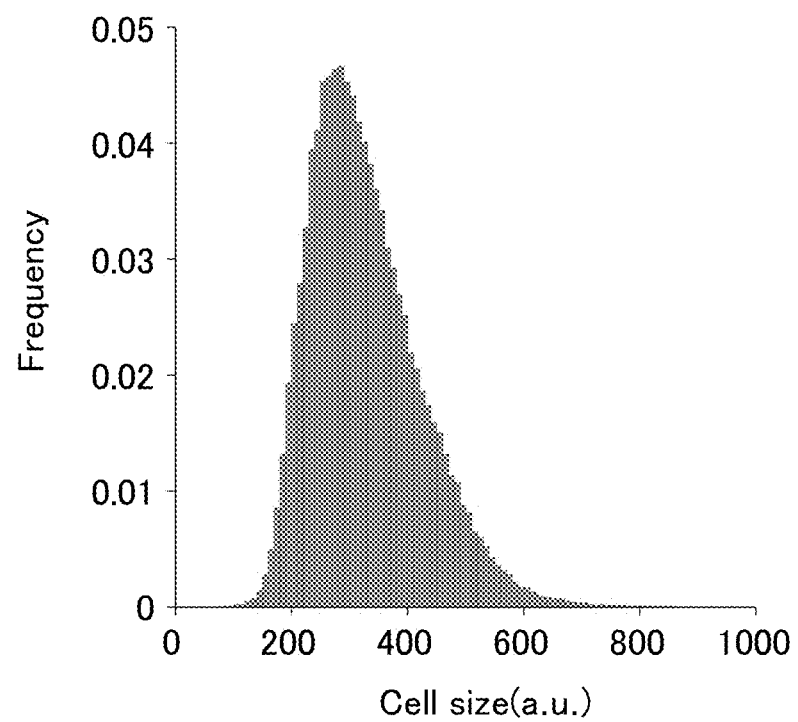
FIG. 10 It is a graph showing a result of a measurement of a frequency distribution of the cell size, by a time-lapse observation of the GFP-expressing E. coli (Example 5).

In the time-lapse observation in Example 4, the frequency distribution of the cell size was measured. The result is shown in FIG. 10.

Example 6

Frequency Distribution of Growth Rate

Figure 11:
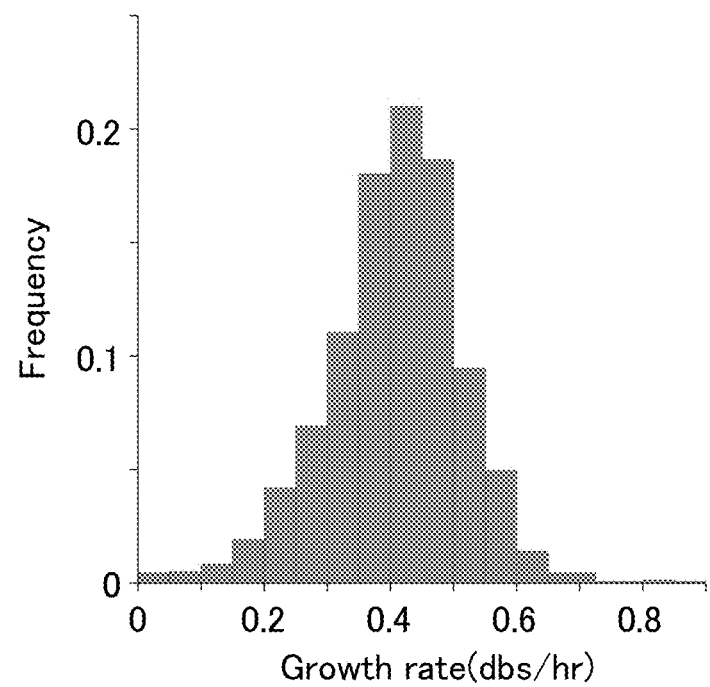
FIG. 11 It is a graph showing a result of a measurement of a frequency distribution of the growth rate, by a time-lapse observation of the GFP-expressing E. coli (Example 6).

In the time-lapse observation in Example 4, the frequency distribution of the growth rate was measured. The growth rate of one cell was obtained by fitting the change in cell size from a division to the next division with an exponential function, $C \times 2^{kt}$, and the exponent k was taken to be the growth rate of each cell. In this expression, C represents a constant, and t represents a time. The result is shown in FIG. 11.

Example 7

Distribution of Generation Time

Figure 12:
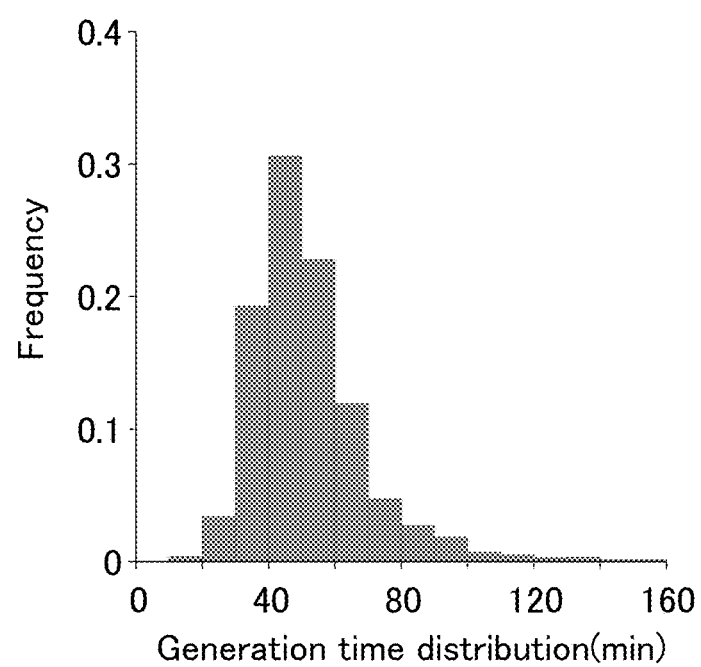
FIG. 12 It is a graph showing a result of a measurement of a frequency distribution of the generation time, by a time-lapse observation of the GFP-expressing E. coli (Example 7).

In the time-lapse observation in Example 4, the frequency distribution of the generation time was measured. The generation time is a time required from a division to the next division for each cell. The result is shown in FIG. 12.

Example 8

Autocorrelation Function of Protein Expression Level

In the time-lapse observation in Example 4, the autocorrelation function of the protein expression level was measured. When a protein expression level at a time point t is let to be x(t), the autocorrelation A(t) relative to a time point that is a time period t after the time point t was calculated according to the following expression.

$$A(\tau) = \frac{E[(x(t) - E[x(t)])(x(t+\tau) - E[x(t)])]}{V[x(t)]} \quad \text{[Chem. 1]}$$

Figure 13:
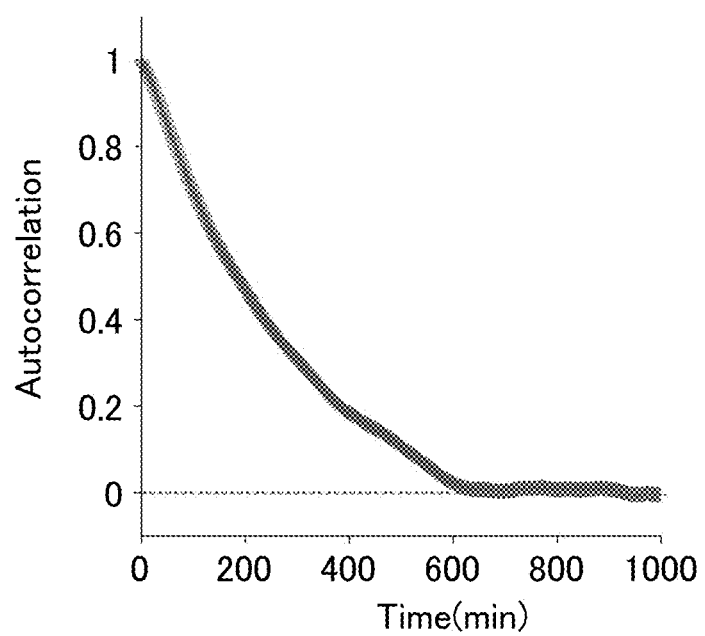
FIG. 13 It is a graph showing a result of a measurement of an autocorrelation function of the protein expression level, by a time-lapse observation of the GFP-expressing E. coli (Example 8).

In this expression, E[ ] and V[ ] represent the expectation and the variance, respectively. The result is shown in FIG. 13. This graph is obtained by plotting A(τ) against τ.

Example 9

Distribution of Cell Division Age

Figure 14:
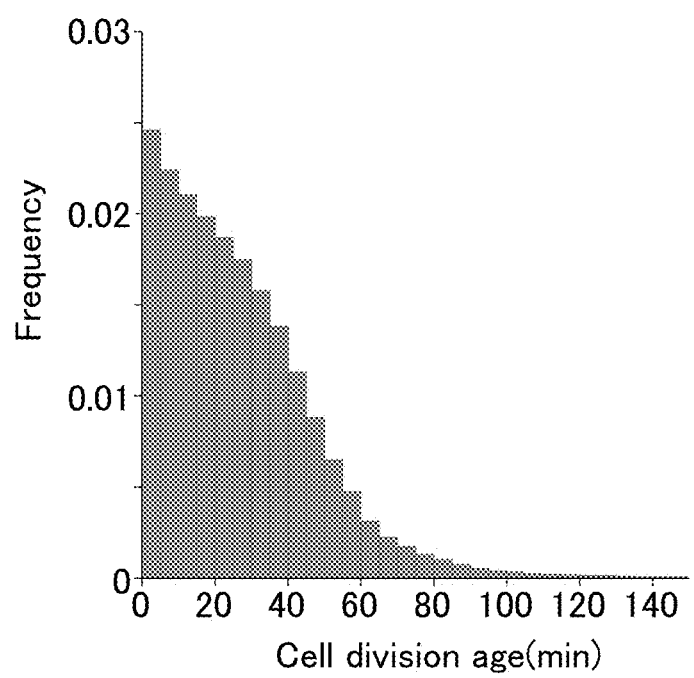
FIG. 14 It is a graph showing a result of a measurement of a frequency distribution of the cell division age, by a time-lapse observation of a GFP-expressing E. coli (Example 9).

In the time-lapse observation in Example 4, the frequency distribution of the cell division age was measured. The cell division age represents a time period from the last division to the present time. The result is shown in FIG. 14.

Example 10

Cell Genealogy Observed in One Observation Groove

Figure 15:
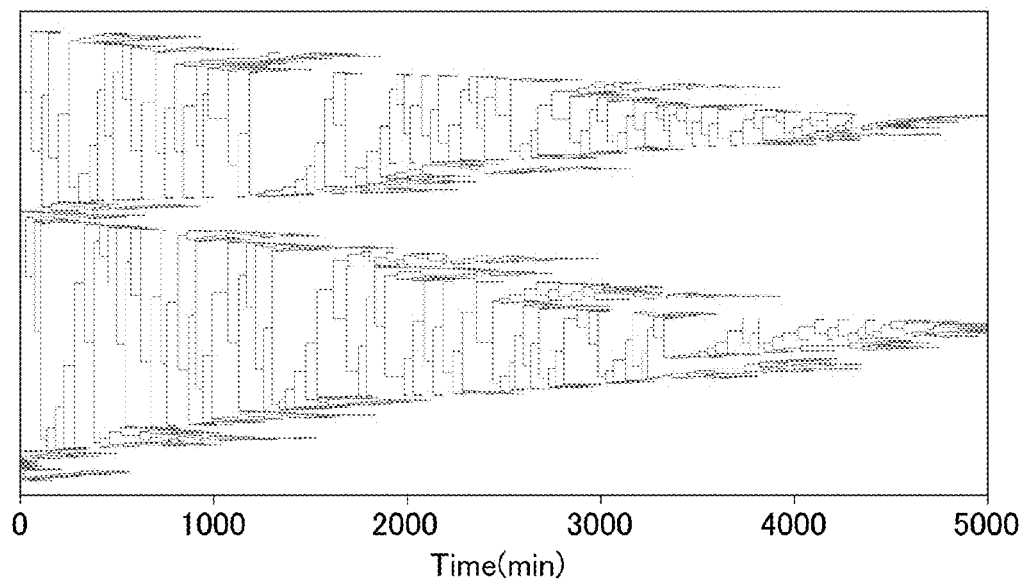
FIG. 15 It is a graph showing a result of a measurement of a cell genealogy observed in one observation groove, by a time-lapse observation of a GFP-expressing E. coli (Example 10).

In the time-lapse observation in Example 4, the cell genealogy observed in one observation groove was measured. The result is shown in FIG. 15. A branch in a system line represents a cell division, and a break of a system line indicates that the cells were washed out.

Example 11

A cell culture apparatus including a cell culture substrate, a PDMS liquid feeding pad, a syringe (liquid feeding pump) and a waste liquid tank, similar as in Example 3, was placed on a stage of an inverted electric microscope, and a time-lapse observation was performed for cells in the culture grooves. Replacing the *E. coli* in the Example 3 with mouse ES cells, a serum-free medium for maintaining the undifferentiated state, ESF7, in place of M9 minimal medium for *E. coli* culture, was allowed to flow continuously with the syringe pump at a flow rate of 2 ml/hr. The surface of the glass substrate was coated with collagen or E cadherin-Fc for facilitating adhesion to the mouse ES cells. The time-lapse observation of the mouse ES cells in the culture grooves was performed at 15 minute intervals by an inverted electric microscope using a phase contrast objective lens of 20 times magnification.

As a result, a state was confirmed where, when culture solution is supplied to the cell culture substrate for continuous culture, a part of the mouse ES cells present at the both ends of a culture groove, among the mouse ES cells present in the culture groove, was moderately washed out to the flow grooves.

Furthermore, it was also confirmed that the mouse ES cells were held and cultured in the culture grooves L stably due to the groove shape of the cell culture substrate and the semipermeable membrane.

It was confirmed that a stable and uniform environment of the interior of the culture grooves L is maintained due to the supply of the culture solution to the mouse ES cells through the semipermeable membrane, and the number of the mouse ES cells in the culture grooves L can be maintained to a prescribed number by the mouse ES cells present at the both ends of the culture grooves being moderately washed out to the flow grooves, and thus enabling continuous culture and observation of the cells. It was also confirmed that the stay of the mother cells in the culture grooves L can be avoided, thereby enabling the long-term culture of the mouse ES cells in the culture grooves L without any variation of physiological state associated with aging.

Comparative Example 1

Culture grooves L having a groove depth L1 smaller than the cell size was formed on a surface of a glass substrate, and a study whether an *E. coli* culture is possible or not was carried out. Specifically, 50 culture grooves L (groove depth L1: 0.5 μm, groove width L2: 2.0 μm, length: 30 μm) and 20 flow grooves M (groove depth M1: 17 μm, groove width M2: 60 μm, length: 5000 μM) were formed in a lattice shape.

Then, the cell culture substrate was covered with a semipermeable membrane similarly as in Example 2, and culture solution was supplied to the cell culture substrate with an apparatus configuration similar as in Example 3, thereby observing the cells.

Figure 16:
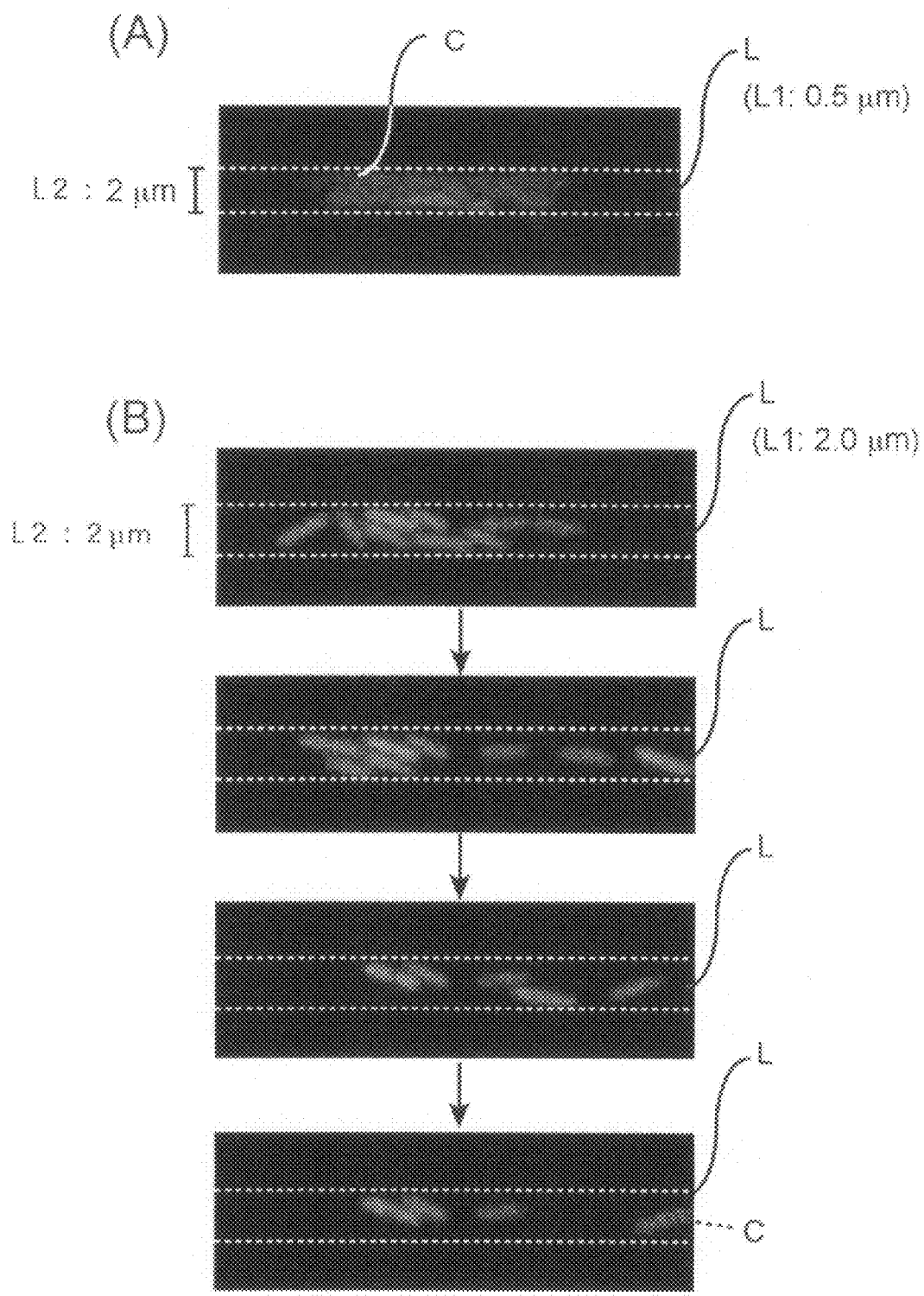
FIG. 16 (A) is a photograph showing a state of cells viewed from the upper side of a glass substrate, in the case of forming a culture groove having a groove depth smaller than the cell size, on the surface of the glass substrate, and (B) is a photograph showing a state of cells viewed from the upper side of a glass substrate, in the case of forming a culture groove having a groove depth equal to or more than twice as large as the cell size, on the surface of the glass substrate.

As a result, the cells C in the culture grooves L were crushed and deformed by the semipermeable membrane, as shown in FIG. 16(A), and thus the observation was not possible in a normal state.

Comparative Example 2

Culture grooves L having a groove depth L1 of more than twice as large as the cell size was formed on a surface of a glass substrate, and a study whether an *E. coli* culture is possible or not was carried out. Specifically, 50 culture grooves L (groove depth L1: 2.0 μm, groove width L2: 2.0 μm, length: 30 μm) and 20 flow grooves M (groove depth M1: 17 μm, groove width M2: 60 μm, length: 5000 μm) were formed in a lattice shape.

Then, the cell culture substrate was covered with a semipermeable membrane similarly as in Example 2, and culture solution was supplied to the cell culture substrate with an apparatus configuration similar as in Example 3, thereby observing the cells.

As a result, cells C were not stably held in the culture grooves L and flowed out from the culture grooves L to the flow grooves M, as shown in FIG. 16(B), and it was confirmed that the continuous culture is difficult.

DESCRIPTION OF THE NUMERALS

1 Cell culture apparatus
1*a* Apparatus for long-term observation of cell culture
2 Cell culture substrate
3 Semipermeable membrane
4 Supply means
5 Microscope observation means
41 Liquid feeding pump
42 Liquid feeding pad
43 Waste liquid tank
44 Foam trapping groove
51*a* Bright field observation light source
51*b* Fluorescent observation light source
52*a* Automatic shutter
52*b* Automatic shutter
53 Condenser lens
54 Dichroic mirror
55 Objective lens
56 XY Stage
57 Camera
58 Computer
L Culture groove
M Flow groove
A Opening
S Frame seal

The invention claimed is:
1. A cell culture apparatus for culturing cells, comprising a cell culture substrate, a semipermeable membrane, a liquid feeding pad and a culture solution supply means, wherein
the cell culture substrate comprises:
(1) a culture groove capable of holding and culturing the cells, wherein the culture groove has a depth 1 to 2 times the size of a desired cell and a width 1 to 3 times the size of the desired cell,
(2) a first flow groove having a width 10 to 100 times the width of the culture groove and a depth 1.5 to 50 times the depth of the culture groove, wherein a side of the first flow groove is attached to a first end of the culture groove at an angle of the flow groove relative to the culture groove of 90°±15°, and
(3) a second flow groove having a width 10 to 100 times the width of the culture groove and a depth 1.5 to 50 times the depth of the culture groove, wherein a side of the second flow groove is attached to a second end of the culture groove at an angle of the flow groove relative to the culture groove of 90°±15°;
the semipermeable membrane covers the culture groove and the flow grooves of the cell culture substrate;
the liquid feeding pad is disposed on the substrate and forms a space over the culture groove, the first and second flow grooves and the semipermeable membrane, and the liquid feeding pad is adhered to a periphery of an area of the substrate comprising the culture groove and the first and second flow grooves;

the culture solution supply means includes a liquid feeding pump and a waste liquid tank; and the cell culture apparatus is configured to continuously culture cells for 200 generations or more by continuously supplying culture solution through the first and second flow grooves to the culture groove and continuously removing culture solution and a portion of cells from the first and second ends of the culture groove through the first and second flow grooves to the waste liquid tank.

2. The cell culture apparatus according to claim 1, wherein the semipermeable membrane is bound to the cell culture substrate via biotin-avidin binding.

3. The cell culture apparatus according to claim 1, wherein the culture solution supply means includes a liquid feeding pad.

4. An apparatus for long-term observation of cell culture, comprising the cell culture apparatus according to claim 1 and a microscope observation means capable of observing cells on the cell culture substrate.

5. The apparatus for long-term observation of cell culture according to claim 4, wherein the microscope observation means is an inverted microscope.

6. A method for long-term observation of cell culture with the apparatus for long-term observation of cell culture according to claim 4, comprising the steps of:

holding cells in the culture groove of the cell culture substrate, covering the culture groove and the flow grooves of the cell culture substrate with the semipermeable membrane, continuously feeding culture solution to the cell culture substrate by the supply means to supply culture solution to cells held in the culture groove of the cell culture substrate through the semipermeable membrane, while discarding a portion of the cells in the culture groove to the flow grooves by culture solution flowing in the flow grooves connected to both ends of the culture groove, and observing the cells on the cell culture substrate by the microscope observation means.

7. A method for long-term cell culture with the cell culture apparatus according to claim 1, comprising the steps of:

holding cells in the culture groove of the cell culture substrate, covering the culture groove and the flow grooves of the cell culture substrate with the semipermeable membrane, and continuously feeding culture solution to the cell culture substrate by the supply means to supply culture solution to cells held in the culture groove of the cell culture substrate through the semipermeable membrane, while discarding a portion of the cells in the culture groove to the flow grooves by culture solution flowing in the flow grooves connected to both ends of the culture groove.

8. An apparatus for long-term observation of cell culture, comprising the cell culture apparatus according to claim 2 and a microscope observation means capable of observing cells on the cell culture substrate.

9. The apparatus for long-term observation of cell culture according to claim 8, wherein the microscope observation means is an inverted microscope.

10. A method for long-term observation of cell culture with the apparatus for long-term observation of cell culture according to claim 8, comprising the steps of:

holding cells in the culture groove of the cell culture substrate, covering the culture groove and the flow grooves of the cell culture substrate with the semipermeable membrane, continuously feeding culture solution to the cell culture substrate by the supply means to supply culture solution to cells held in the culture groove of the cell culture substrate through the semipermeable membrane, while discarding a portion of the cells in the culture groove to the flow grooves by culture solution flowing in the flow grooves connected to both ends of the culture groove, and observing the cells on the cell culture substrate by the microscope observation means.

11. An apparatus for long-term observation of cell culture, comprising the cell culture apparatus according to claim 3 and a microscope observation means capable of observing cells on the cell culture substrate.

12. The apparatus for long-term observation of cell culture according to claim 11, wherein the microscope observation means is an inverted microscope.

13. A method for long-term observation of cell culture with the apparatus for long-term observation of cell culture according to claim 11, comprising the steps of:

holding cells in the culture groove of the cell culture substrate, covering the culture groove and the flow grooves of the cell culture substrate with the semipermeable membrane, continuously feeding culture solution to the cell culture substrate by the supply means to supply culture solution to cells held in the culture groove of the cell culture substrate through the semipermeable membrane, while discarding a portion of the cells in the culture groove to the flow grooves by culture solution flowing in the flow grooves connected to both ends of the culture groove, and observing the cells on the cell culture substrate by the microscope observation means.

* * * * *